(12) United States Patent
Aggarwal (10) Patent No.: US 7,105,576 B2
(45) Date of Patent: *Sep. 12, 2006

(54) SYNERGISTIC EFFECTS OF NUCLEAR TRANSCRIPTION FACTOR NF-κB INHIBITORS AND ANTI-NEOPLASTIC AGENTS

(75) Inventor: Bharat Aggarwal, Houston, TX (US)

(73) Assignee: Research Development Foundation, Carson City, NV (US)

( * ) Notice: Subject to any disclaimer, the term of this patent is extended or adjusted under 35 U.S.C. 154(b) by 337 days.

This patent is subject to a terminal disclaimer.

(21) Appl. No.: 10/422,292

(22) Filed: Apr. 24, 2003

(65) Prior Publication Data

US 2004/0002499 A1    Jan. 1, 2004

Related U.S. Application Data

(60) Provisional application No. 60/375,288, filed on Apr. 24, 2002.

(51) Int. Cl.
*A61K 31/12* (2006.01)
*A01N 35/00* (2006.01)

(52) U.S. Cl. .................................. 514/679
(58) Field of Classification Search ............ None
See application file for complete search history.

(56) References Cited

U.S. PATENT DOCUMENTS

| | | | |
|---|---|---|---|
| 5,891,924 A | 4/1999 | Aggarwal | 514/679 |
| 2001/0025034 A1 | 9/2001 | Arbiser | 514/114 |
| 2002/0019382 A1 | 2/2002 | Snyder et al. | 514/210.2 |
| 2002/0035090 A1 | 3/2002 | Zeldis | 514/58 |
| 2004/0058021 A1 | 3/2004 | Aggarwal | 424/756 |
| 2005/0049299 A1 | 3/2005 | Aggarwal | 514/456 |

OTHER PUBLICATIONS

PubMed, Miller et al, Clin Breast Cancer, Oct. 2001 2(3) 236, abstract.*
Medline AN94201161, Arbuck, et al, Hematology/oncology clinics of N Am, 1994.*
Brennan et al., "Inhibition of nuclear factor κB by direct modification in whole cells—mechanism of action of nordihydroguaiaretic acid, curcumin and thiol modifiers," *Biochem. Pharmacol.*, 55:965-973, 1998.
Cheng et al., "Phase I chemoprevention clinical trail of curcumin,," *Proc. Am. Soc. Clin. Oncol.* 17:558a, 1998.
Estrov et al., "Phenylarsine oxide blocks interleukin-1beta-induced activation of the nuclear transcription factor NF-kappaB, inhibits proliferation, and induces apoptosis of acute myelogenous leukemia cells," *Blood*, 94:2844-2853, 1999.
Feinman et al., "Role of NF-kappaB in the rescue of multiple myeloma cells from glucocorticoid-induced apoptosis by bcl-2," *Blood*, 93:3044-3052, 1999.
Giri and Aggarwal, "Constitutive activation of NF-kappaB causes resistance to apoptosis in human cutaneous T cell lymphoma HuT-78 cells. Autocrine role of tumor necrosis factor and reactive oxygen intermediates," *J. Biol. Chem.*, 273:14008-14014, 1998.
Han et al., "Curcumin causes the growth arrest and apoptosis of B cell lymphoma by downregulation of egr-1, c-myc, bcl-XL, NF-kappa B, and p53," *Clin. Immunol.*, 93:152-161, 1999.
Hour et al., "Curcumin enhances cytotoxicity of chemotherapeutic agents in prostate cancer cells by inducing p21(WAF1/CIP1) and C/EBPbeta expressions and suppressing NF-kappaB activation," *Prostate*, 51:211-218, 2002.
Huang et al., "Effect of dietary curcumin and dibenzoylmethane on formation of 7,12-dimethylbenz[a]anthracene-induced mammary tumors and lymphomas/leukemias in Sencar mice," *Carcingenesis*, 19:1697-1700, 1998.
Ichiki et al., "Regulation of activator protein-1 activity in the mediastinal lymph node metastasis of lung cancer," *Clin. Exp. Metastasis*, 18:539-545, 2001.
Inano et al., "Chemoprevention by curcumin during the promotion stage of tumorigenesis of mammary gland in rats irradiated with gamma-rays," *Carcingenesis*, 20:1011-1018, 1999.
Jaffe et al., "Adjuvant methotrexate and citrovorum-factor treatment of osteogenic sarcoma," *N. Engl. J. Med.*, 291:994-997, 1974.
Jang et al., "A curcuminoid and sesquiterpenes as inhibitors of macrophage TNF-alpha release from Curcuma zedoaria," *Planta Med.* 67:550-552, 2001.
Jaruga et al., "Apoptosis-like, reversible changes in plasma membrane asymmetry and permeability, and transient modifications in mitochondrial membrane potential induced by curcumin in rat thymocytes," *FEBS Lett.*, 433(3):287-293, 1998.
Jobin et al., "Curcumin blocks cytokine-mediated NF-kappa B activation and proinflammatory gene expression by inhibiting inhibitory factor I-kappa B kinase activity," *J. Immunol.*, 163:3474-3483, 1999.
Kawamori et al., "Chemopreventive effect of curcumin, a naturally occurring anti-inflammatory agent, during the promotion/progression stages of colon cancer," *Cancer Res.* 59:597-601, 1999.
Kumar et al., "Curcumin (Diferuloylmethane) inhibition of tumor necrosis factor (TNF)-mediated adhesion of monocytes to endothelial cells by suppression of cell surface expression of adhesion molecules and of nuclear factor-kappaB activation," *Biochem. Pharmacol.*, 55:775-783, 1998.
Mehta et al., "Antiproliferative effect of curcumin (diferuloylmethane) against human breast tumor cell lines," *Anti-Cancer Drugs*, 8:470-481, 1997.
Menon et al, "Anti-metastatic activity of curcumin and catechin," *Cancer Lett.*, 141:159-165, 1999.

(Continued)

*Primary Examiner*—Christopher S. F. Low
*Assistant Examiner*—Shirley V. Gembeh
(74) *Attorney, Agent, or Firm*—Fulbright & Jaworski L.L.P.

(57) ABSTRACT

The present invention provides methods of inhibiting metastasis of a tumor and methods of treating a tumor using a combination of an inhibitor of the activation of nuclear factor NF-κB and a cancer chemotherapeutic agent. In one embodiment of the present invention, combination of curcumin and paclitaxel (taxol) can be used to treat and inhibit metastasis of breast tumor.

24 Claims, 5 Drawing Sheets

OTHER PUBLICATIONS

Mohan et al., "Curcuminoids inhibit the angiogenic response stimulated by fibroblast growth factor-2, including expression of matrix metalloproteinase gelatinase B," *J. Biol. Chem*, 275:10405-10412,2000.

Navis et al., "Dietary curcumin with cisplatin administration modulates tumour marker indices in experimental fibrosarcoma," *Pharmacol. Res.*, 39:175-179, 1999.

Ni et al., "Analysis of expression of nuclear factor kappa B (NF-kappa B) in multiple myeloma: downregulation of NF-kappa B induces apoptosis," *Br. J. Haematol.* 115:279-286, 2001.

Pahl et al., "Activators and target genes of Rel/NF-kappaB transcription factors," *Oncogene*, 18:6853-6866, 1999.

Pan et al., "Comparative studies on the suppression of nitric oxide synthase by curcumin and its hydrogenated metabolites through down-regulation of IkappaB kinase and NFkappaB activation in macrophages," *Biochem. Pharmacol.*, 60:1665-1676, 2000.

Plummer et al., "Inhibition of cyclo-oxygenase 2 expression in colon cells by the chemopreventive agent curcumin involves inhibition of NF-kappaB activation via the NIK/IKK signalling complex," *Oncogene*, 18:6013-6020, 1999.

Podar et al., "Essential role of caveolae in interleukin-6- and insulin-like growth factor I-triggered Akt-1-mediated survival of multiple myeloma cells," *J. Biol. Chem.*, 278(8):5794-801, 2002.

Ramachandran et al., "Differential sensitivity of human mammary epithelial and breast carcinoma cell lines to curcumin," *Breast Cancer Res. and Treat.*, 54:269-278, 1999.

Rao et al., "Chemoprevention of colon carcinogenesis by dietary curcumin, a naturally occurring plant phenolic compound," *Cancer Res.*, 55:259-266, 1995.

Shishodia and Aggarwal, "Nuclear factor-B activation: a question of life and death," *J. Biochem Mol. Biol.*, 35:28-40, 2002.

Simon et al., "Inhibitory effect of curcuminoids on MCF-7 cell proliferation and structure-activity relationships," *Cancer Lett.*, 129:111-116, 1998.

Singh and Aggarwal, "Activation of transcription factor NF-kappa B is suppressed by curcumin (diferuloylmethane)" *J. Biol Chem.*, 270:24995-25000, 1995.

Singletary et al., "Inhibition of 7,12-dimethylbenz[a]anthracene (DMBA)-induced mammary tumorigenesis and DMBA-DNA adduct formation by curcumin," *Cancer Lett.*, 103:137-141, 1996.

Sonneveld et al., "Cyclosporin A combined with vincristine, doxorubicin and dexamethasone (VAD) compared with VAD alone in patients with advanced refractory multiple myeloma: an EORTC-HOVON randomized phase III study (06914)," *Br. J. Haematol.*, 115(4):895-902.

Westerheide et al., "The putative oncoprotein Bcl-3 induces cyclin D1 to stimulate G(1) transitiion" *Mol. Cell. Biol.* 21:8428-8436, 2001.

Zhang et al., "" Zhongguo Yaolixue Tongbao, 17(6):702-704, 2001 (Abstract).

Zhang et al., "Curcumin inhibits cyclooxygenase-2 transcription in bile acid- and phorbol ester-treated human gastrointestinal epithelial cells," *Carcinogenesis,* 20:445-451, 1999.

Zhang et al., "Tyrosine kinase inhibitor emodin suppresses growth of HER-2/neu-overexpressing breast cancer cells in athymic mice and sensitizes these cells to the inhibitory effect of paclitaxel," *Clin. Cancer Res.*, 5:343-353, 1999.

\* cited by examiner

SYNERGISTIC EFFECTS OF NUCLEAR TRANSCRIPTION FACTOR NF-κB INHIBITORS AND ANTI-NEOPLASTIC AGENTS

CROSS-REFERENCE TO RELATED APPLICATION

This non-provisional patent application claims benefit of provisional patent application 60/375,288, filed Apr. 24, 2002, now abandoned.

BACKGROUND OF THE INVENTION

1. Field of the Invention

The present invention relates generally to the field of cancer treatment. More specifically, the present invention relates to the unexpected synergistic effects of nuclear transcription factor NF-κB inhibitors and anti-neoplastic agents in the treatment of cancer.

2. Description of the Related Art

Every year breast cancer is diagnosed in 910,000 women worldwide, and 376,000 women die from the disease (1). Most of these cases are in industrialized countries with 180,000 in North America and 220,000 in Europe. The highest reported rates of breast cancer incidence are for white or Hawaiian women in the United States and the rates in Africa and Asia are significantly lower (1). Immigrants from low-risk to high-risk regions experience rates of breast cancer incidence approaching those of the host country, suggesting lifestyle is the major contributor to the development of the disease. Only 5% of the cases have been assigned to inherited mutations in genes such as BRCA1 and BRCA2, while diet and environment may be responsible for as many as 50% of breast cancers (2).

Although the precise nature of the lifestyle risk factors causative for breast cancer are unknown, some of the known ones are age, race, ethnicity, hormones, and dietary factors (3, 4). Epidemiological and animal studies have shown that different microchemicals present in the diet could be effective agents for the prevention of cancer incidence and mortality (2, 5–6).

The induction of most cancers, for example breast cancer, is a multistep process initiated with DNA damage and followed by alteration of different signaling pathways. Usually, at the initial stages, breast cancer is hormone-dependent, relying on natural steroids. In later stages, however, growth of breast cancer becomes hormone-independent (7). Approximately 40% of the patients diagnosed with breast cancer have disease that has regional or distant metastases and, at present, there is no efficient curative therapy for breast cancer patients with advanced metastatic disease.

Paclitaxel (taxol), derived from the Pacific yew tree, is the first taxane used in clinical practice, and has shown a significant amount of anti-tumor activity in patients with breast cancer, ovarian cancer, head and neck cancer, non-small-cell lung cancer and sarcoma (8, 9). Taxanes represent a new class of antitumor agents that exert their action by promoting tubulin polymerization and microtubule assembly. Paclitaxel has been shown to induce in vitro apoptosis in various breast tumor cell lines and the degree of apoptosis inversely correlates with expression of HER2 in these cell lines (10, 11). How paclitaxel induces apoptosis is not fully understood (12), but a number of apoptosis-associated genes that either suppress, activate or mediate apoptosis are affected by paclitaxel. Tyrosine phosphorylation (13), microtubule assembly (14), bcl-2 phosphorylation (15), bcl-xl (16), p21, and p53 (17) have been implicated.

In addition to activating the apoptosis pathway, paclitaxel also simultaneously activates the anti-apoptotic pathway through induction of NF-κB in macrophages (18), ovarian cells (19), lung cancer cells (20), and breast tumor cells (21). The NF-κB activation by paclitaxel leads to the expression of various genes including interleukin-8 (19, 20), IL-1, and TNF (22). Expression of IL-8 can either enhance growth as in the case of melanoma (23), or promote angiogenesis as in the case of human lung carcinoma (24). Several groups have shown that NF-κB activation could lead to suppression of apoptosis (25–28). Paclitaxel-induced apoptosis in leukemia cells is suppressed by the activation of NFκB (28). NF-κB has been shown to directly activate the expression of bcl-xl (29), and bcl-xl over-expression has been shown to suppress paclitaxel-induced apoptosis. Paclitaxel is also known to activate JNK and AP-1, which could contribute to its anti-apoptotic pathway (30).

NF-κB plays an essential role in the development and progression of breast cancer. Animal studies suggest the presence of constitutively active NF-κB at an early stage during neoplastic transformation of mammary cells (31). NF-κB inhibits apoptosis in mouse mammary epithelia (32) and selective activation of NF-κB subunits have been found in human breast cancer cell lines and patient samples (33, 34). An inverse correlation between the levels of NF-κB activation and estrogen receptor expression has been reported (35) and inhibition of NF-κB in breast cancer cells induces spontaneous apoptosis (32, 34). Paclitaxel-induced sensitivity of breast cancer cell lines was enhanced by an NF-κB inhibitor, parthenolide (36, 37). The Mullerian inhibiting substance was also found to inhibit breast cancer growth through NF-κB mediated pathway (38). Furthermore, the transactivation function of NF-κB is negatively regulated by IκBβ1 in breast cancer cell lines (37). Lastly, overexpression of HER2/neu can activate NF-κB through the activation of Akt pathway and block apoptosis (39). All these reports together suggest that NF-κB may play an important role in breast cancer.

Curcumin (diferuloylmethane), a non-nutritive food chemical present in turmeric (*Curcuma longa*), has been found to be pharmacologically safe as indicated by consumption of curcumin as a dietary spice for centuries at doses up to 100 mg/day (40). Curcumin has been shown to block tumor initiation induced by benzo [a] pyrene and 7, 12 dimethylbenz [a] anthracene (41) and to suppress phorbol ester-induced tumor promotion (42, 43). Curcumin was found to suppress carcinogenesis of skin (43–47), forestomach (48, 49), colon (50–52), and liver (53) in mice. Curcumin has also been shown to suppress mammary carcinogenesis (54–56). Curcumin exhibits a number of characteristics that indicate curcumin would have potent chemopreventive activity. These characteristics are set forth below.

Curcumin Exhibits Antiproliferative Effects Against Tumor Cells

Curcumin has been shown to inhibit the proliferation of a wide variety of tumor cells including B cell and T cell leukemia (57–60), colon carcinoma (61), and epidermoid carcinoma (62). It has also been shown to suppress the proliferation of various breast carcinoma cell lines in culture (63–65). Growth of the breast tumor cell lines BT20, SKBR3, MCF-7, T47D, and ZR75-1 were completely inhibited by curcumin as indicated by MTT dye uptake, thymidine incorporation, and clonogenic assay (63). Curcumin can overcome adriamycin resistance in MCF-7 cells (63). Recently, curcumin was shown to activate caspase-8 which leads to cleavage of BID, thus resulting in sequential release of mitochondrial cytochrome C and activation of caspase-9 and caspase-3 (66).

Curcumin Downregulates the Activity of EGFR and Expression of HER2/neu

Effects on HER2/neu and EGFR may represent one possible mechanism by which curcumin suppresses the growth of breast cancer cells. Almost 30% of the breast cancer cases have been shown to overexpress the HER2/neu protooncogene (67), and both HER2 and EGF receptors stimulate proliferation of breast cancer cells. Overexpression of these two proteins correlates with progression of human breast cancer and poor patient prognosis (67). Curcumin has been shown to downregulate the activity of EGFR (62, 68) and HER2/neu (69) and to deplete the cells of HER2/neu protein (69). Additionally, curcumin can downregulate bcl-2 expression, which may contribute to its antiproliferative activity (70).

Curcumin Downregulates the Activation of Nuclear Factor-κB

Curcumin may also operate through NF-κB. NF-κB is a nuclear transcription factor required for the expression of genes involved in cell proliferation, cell invasion, metastasis, angiogenesis, and resistance to chemotherapy (71). This factor is activated in response to inflammatory stimuli, carcinogens, tumor promoters, and hypoxia which is frequently encountered in tumor cells (72). Activated NF-κB suppresses apoptosis in a wide variety of tumor cells (25–27), and it has been implicated in chemoresistance (25). Cells that overexpress NF-κB are resistant to paclitaxel-induced apoptosis (28). Furthermore, the constitutively active form of NF-κB has been reported in human breast cancer cell lines in culture (35), carcinogen-induced mouse mammary tumors (73), and biopsies from patients with breast cancer (33). Various tumor promoters, including phorbol ester, TNF and $H_2O_2$ activate NF-κB and that curcumin downregulates the activation (74). Subsequently, others showed that curcumin-induced downregulation of NF-κB is mediated through suppression of IκBα kinase activation (75, 76).

Curcumin Downregulates the Activation of AP-1 and c-jun Kinase

AP-1 is another transcription factor that has been closely linked with proliferation and transformation of tumor cells (77). The activation of AP-1 requires the phosphorylation of c-jun through activation of stress-activated kinase c-jun N-terminal kinase (JNK) (78). The activation of JNK is also involved in cellular transformation (79). Curcumin has been shown to inhibit the activation of AP-1 induced by tumor promoters (80) and JNK activation induced by carcinogens (81).

Curcumin Suppresses the Induction of Adhesion Molecules

The expression of various cell surface adhesion molecules such as ICAM-1, VCAM-1 and ELAM-1 on endothelial cells are absolutely critical for tumor metastasis (82). The expression of these molecules is in part regulated by nuclear factor NF-κB (83). Treatment of endothelial cells with curcumin blocks the cell surface expression of adhesion molecules and this accompanies the suppression of tumor cell adhesion to endothelial cells (84). Downregulation of these adhesion molecules is mediated through the downregulation of NF-κB activation (84).

Curcumin Downregulates Cox2 Expression

Overexpression of cyclooxygenase (COX)-2 has been shown to be associated with a wide variety of cancers, including colon (85), lung (86), and breast (87) cancers. The role of COX2 in suppression of apoptosis and tumor cell proliferation has been demonstrated (88). Furthermore, celebrex, a specific inhibitor of COX2, has been shown to suppress mammary carcinogenesis in animals (89). Several groups have shown that curcumin downregulates the expression of COX2 protein in different tumor cells (76, 90), most likely through the downregulation of NF-κB activation (76), which is needed for COX2 expression.

Curcumin Inhibits Angiogenesis

For most solid tumors, including breast cancer, angiogenesis (blood vessel formation) is essential for tumor growth and metastasis (91). The precise mechanism that leads to angiogenesis is not fully understood, but growth factors that cause proliferation of endothelial cells have been shown to play a critical role in this process. Curcumin has been shown to suppress the proliferation of human vascular endothelial cells in vitro (92) and abrogate FGF-2-induced angiogenic response in vivo (93), thus suggesting curcumin is also an antiangiogenic factor. Indeed curcumin has been shown to suppress angiogenesis in vivo (94).

Curcumin Suppresses the Expression of Matrix Metalloprotease (MMP)-9 and Inducible Nitric Oxide Oxidase (Inos)

MMP-9 is one of the proteases that has been shown to be regulated by NF-κB activation (96), and curcumin has been shown to suppress its expression (96). Curcumin has also been demonstrated to downregulate iNOS expression, also regulated by NF-κB and involved in tumor metastasis (97). All these observations suggest that curcumin must have anti-metastatic activity. Indeed, there is a report suggesting that curcumin can inhibit tumor metastasis (98).

Curcumin Downregulates Cyclin D1 Expression

Cyclin D1, a component subunit of cyclin-dependent kinase (Cdk)-4 and Cdk6, is rate limiting in progression of cells through the first gap (G1) phase of the cell cycle. Aberrant overexpression of cyclin D1 is associated with breast cancer formation, with cyclin D1 mRNA overexpressed in 70–100% of breast cancer cell lines and the majority of breast cancers (99). Targeted overexpression of cyclin D1 induced mammary adenocarcinoma (100), and transgenic mice lacking both cyclin D1 alleles failed to develop normal mammary glands (101). Furthermore cyclin D1 is required for transformation by activated HER2/neu (102). Antisense to cyclin D1 has been shown to induce apoptosis (103). Thus cyclin D1 downregulation has been suggested as one of the target for the treatment of breast cancer. Retinoic acid, a chemopreventive agent, has been shown to diminish cyclin D1 protein but not the mRNA through post-translational regulation (104). Expression of cyclin D1 is also regulated through NF-κB (105). Recent studies indicate that curcumin can rapidly downregulate the expression of cyclin D1 at the transcriptional and post-transcriptional level, and this may contribute to the antiproliferative effects of curcumin against various cell types.

The prior art is deficient in clinical strategies that augment the therapeutic efficacy of existing antineoplastic agents against cancer with a NF-κB-blocking chemopreventive agent. The present invention fulfills this long standing need and desire in the art by demonstrating the efficacy of a combination therapy approach involving an NF-κB blocker such as curcumin.

SUMMARY OF THE INVENTION

It is an object of the present invention to demonstrate synergistic effects of nuclear transcription factor NF-κB inhibitors and anti-neoplastic agents in inhibiting tumor growth and metastasis. In one embodiment of the present invention, synergistic effects of curcumin and the chemotherapeutic agent paclitaxel (taxol) in inhibiting tumor growth and metastasis are disclosed. Curcumin blocks paclitaxel-induced NF-κB activation in breast cancer cells. Furthermore, curcumin augments paclitaxel-induced apoptosis in breast cancer cells and enhances the therapeutic effects of paclitaxel against breast cancer by inhibiting breast cancer metastasis in vivo.

In one embodiment of the present invention, there is provided a method of inhibiting metastasis of a tumor and a method of treating a tumor in an individual in need of such treatment, comprising the step of administering to said individual a pharmacologically effective dose of an inhibitor of the activation of nuclear factor NF-κB and a cancer chemotherapeutic agent.

In another embodiment of the present invention, there are provided a method of inhibiting metastasis of a tumor and a method of treating a tumor in an individual in need of such treatment, comprising the step of administering to said individual a pharmacologically effective dose of curcumin and a cancer chemotherapeutic agent.

In yet another embodiment of the present invention, there are provided a method of inhibiting metastasis of breast tumor and a method of treating breast tumor in an individual in need of such treatment, comprising the step of administering to said individual a pharmacologically effective dose of curcumin and a cancer chemotherapeutic agent.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

It will be apparent to one skilled in the art that various substitutions and modifications may be made to the invention disclosed herein without departing from the scope and spirit of the invention.

As used herein, the term "nuclear factor NF-κB" or "NF-κB" shall refer to the protein specific to B cells that binds to a specific DNA sequence (5'-GGGGACTTTCC-3') (SEQ ID No. 1) within the immunoglobulin light chain κ locus enhancer region, and in mammals it is a heterodimer consisting of p50 and p65 (Rel-A) proteins. NF-κB plays a role in various responses, leading to host defense through rapid induction of gene expression, and controls the expression of various inflammatory cytokines, the major histocompatibility complex genes, and adhesion molecules involved in tumor metastasis.

As used herein, the term "therapeutically effective amount" of an agent shall refer to an amount of that agent which is physiologically significant and improves an individual's health. An agent is "physiologically significant" if its presence results in a change in the physiology of the recipient human. For example, in the treatment of a pathological condition, administration of an agent that relieves or arrests further progress of the condition would be considered both physiologically significant and therapeutically effective.

For the therapeutic applications, a person having ordinary skill in the art of molecular pharmacology would be able to determine, without undue experimentation, the appropriate dosages and routes of administration of the inhibitors of the activation of NF-κB useful in the methods of the present invention.

It is an object of the present invention to demonstrate synergistic effects of nuclear transcription factor NF-κB inhibitors and anti-neoplastic agents in inhibiting tumor growth and metastasis. Representative NF-κB inhibitors include curcumin, CAPE, capsaicin, sanguinarin, PTPase inhibitors, lapachone, resveratrol, vesnarinone, leflunomide, anethole, PI3 kinase inhibitors, oleanderin, emodin, serine protease inhibitors, protein tyrosine kinase inhibitors, thalidomide and methotrexate.

In one embodiment of the present invention, synergistic effects of curcumin and the chemotherapeutic agent paclitaxel (taxol) in inhibiting tumor growth and metastasis are disclosed. Curcumin blocks paclitaxel-induced NF-κB activation in breast cancer cells. Furthermore, curcumin augments paclitaxel-induced apoptosis in breast cancer cells and enhances the therapeutic effects of paclitaxel against breast cancer by inhibiting breast cancer metastasis in vivo. One of ordinary skill in the art would recognize that the synergistic effects of curcumin and paclitaxel disclosed herein could readily be extended to other NF-κB inhibitors and chemotherapeutic agents, and NF-κB inhibitors besides curcumin can be used to manifest the same synergistic effects in inhibiting tumor growth and metastasis.

The present invention is directed to a method of inhibiting metastasis of a tumor and a method of treating a tumor in an individual in need of such treatment, comprising the step of administering to said individual a pharmacologically effective dose of an inhibitor of the activation of nuclear factor NF-κB and a cancer chemotherapeutic agent. Representative inhibitors of the activation of nuclear factor NF-κB include curcumin, CAPE, capsaicin, sanguinarin, PTPase inhibitors, lapachone, resveratrol, vesnarinone, leflunomide, anethole, PI3 kinase inhibitors, oleanderin, emodin, serine protease inhibitors, protein tyrosine kinase inhibitors, thalidomide and methotrexate. Generally, the curcumin is administered in a dose of from about 100 mg/kg to about 1000 mg/kg. Representative tumors which can be treated using this method include breast tumor, prostate, melanoma, pancrease, colon, leukemia and multiple myeloma. Representative cancer chemotherapeutic agents which may be used in this method include paclitaxel, gemcitabin, 5-Flurouracil, etoposide, cisplatin, campothecin, vincristine and doxorubicin.

The present invention is also directed to a method of inhibiting metastasis of a tumor and a method of treating a tumor in an individual in need of such treatment, comprising the step of administering to said individual a pharmacologically effective dose of curcumin and a cancer chemotherapeutic agent. Representative tumors which can be treated using this method and representative cancer chemotherapeutic agents that may be used in this method are listed above.

The present invention is also directed to a method of inhibiting metastasis of a breast tumor and a method of treating breast tumor in an individual in need of such treatment, comprising the step of administering to said individual a pharmacologically effective dose of curcumin and a cancer chemotherapeutic agent. Representative cancer chemotherapeutic agents that may be used in this method are listed above.

The following examples are given for the purpose of illustrating various embodiments of the invention and are not meant to limit the present invention in any fashion.

EXAMPLE 1

Paclitaxel-Induced NF-κB Activation in Breast Cancer Cell

To demonstrate that curcumin inhibits paclitaxel-induced NF-κB activation in breast cancer cells, it is essential to know how paclitaxel activates NF-κB. Although several reports have demonstrated that paclitaxel activates NF-κB in different cell types, the mechanism is not understood (18–21). While most reports showed NF-κB activation by paclitaxel within 30 minutes (18–20), a recent report showed activation at 12 hours (21). Whether paclitaxel-induced NF-κB activation occurs through the activation of IκBα kinase (IKK) and phosphorylation of IκBα is also not known.

The upstream signaling elements to IKK through which paclitaxel activates NF-κB are known. TNF-induced NF-κB activation is mediated through sequential recruitment of the TNF receptor, TRADD, TRAF2, NIK and IKK (106). Different agents activate NF-κB through different mechanisms (107). For instance, TNF-induced NFκB activation requires phosphorylation of IκBα at serine 32 and 36, pervanadate-induced NF-κB activation requires tyrosine 42 phosphorylation of IκBα (107). Whether paclitaxel-induced NF-κB activation follows a similar pathway has not been established. All this information is essential to establish whether curcumin blocks paclitaxel-induced NF-κB activation and how curcumin blocks the activation. There are reports to suggest that the mechanism may vary from one cell type to another (108).

Figure 1:
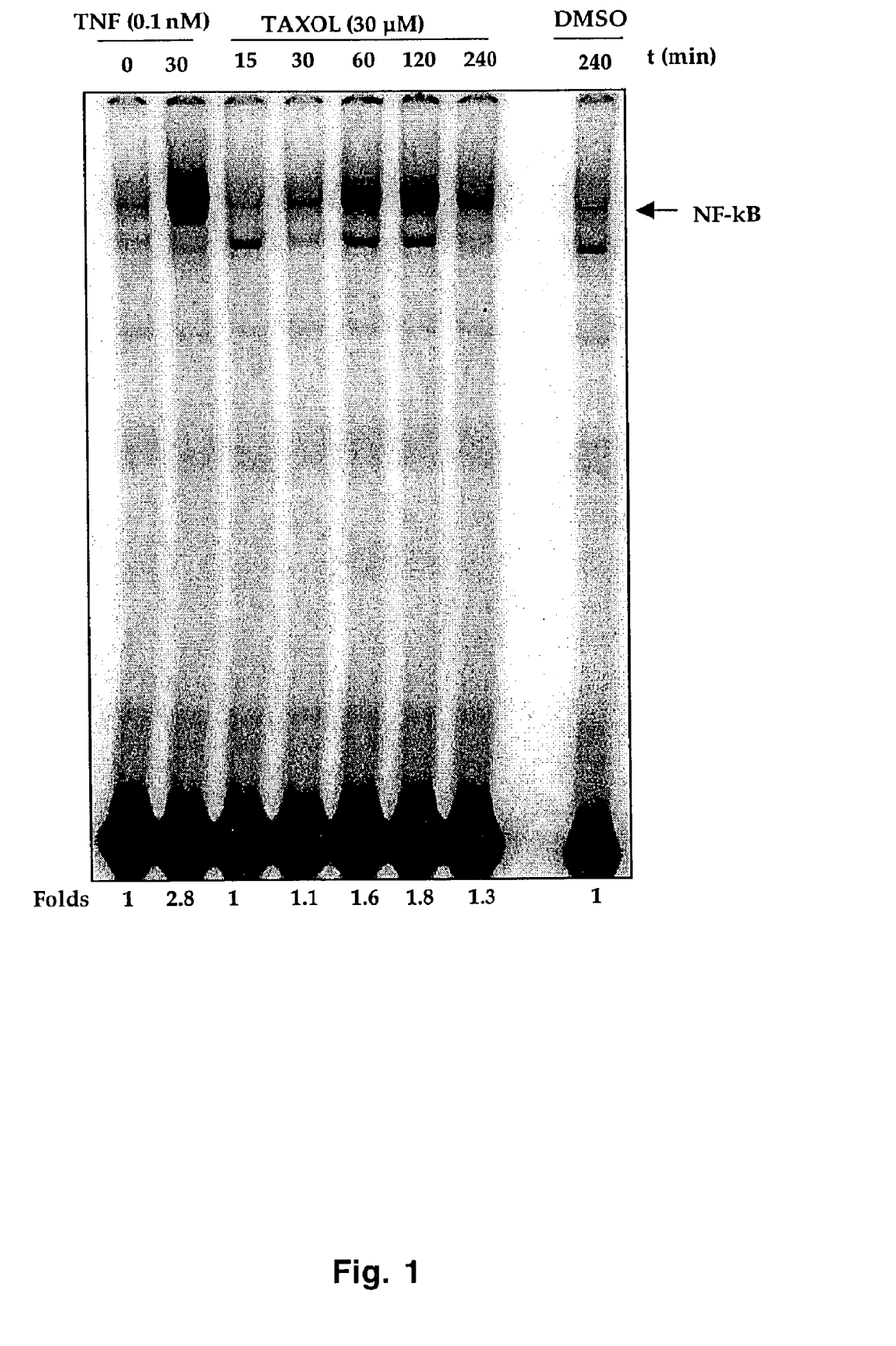
FIG. 1 shows the effect of paclitaxel (Taxol) on NF-κB activation. MCF-7 cells ($1 \times 10^6$ cells/ml) were incubated with Taxol (30 μM) for different time periods and tested for NF-κB activation. Cells treated with 0 and 0.1 nM TNF were included as negative and positive control respectively.

To examine the effect of paclitaxel on activation of NF-κB and IκBα phosphorylation and degradation in breast cancer cell lines, human breast adenocarcinoma MCF-7 cells can be treated with increasing concentrations of paclitaxel for different time periods. Nuclear and cytoplasmic extracts can then be prepared as previously described (109). The nuclear extracts can be analyzed for NF-κB by electrophoretic mobility shift assay (EMSA) as shown in FIG. 1, and cytoplasmic extracts can be analyzed for IκBα phosphorylation and degradation as previously described (109, 110). The cytoplasmic extracts can also be analyzed for the activation of IKK using an immune complex kinase assay as described (110). The activation of NF-κB can also be examined by using NF-κB-dependent reporter gene transcription as previously described (111). Whether paclitaxel-induced NF-κB activation is inhibited by plasmids containing dominant-negative form of TRAF2, NIK, IKK or IκBα can also be examined using methodology well known to one of ordinary skill in the art. These experiments would provide sufficient information about the mechanism of paclitaxel-induced NF-κB activation in breast cancer cells.

EXAMPLE 2

Suppression of Paclitaxel-Induced NF-κB Activation by Curcumin

Curcumin suppresses NF-κB activation induced by TNF, $H_2O_2$ and phorbol ester in myeloid (74) and endothelial cells (84). Different agents activate NF-κB through different mechanisms (106–108). Curcumin blockade paclitaxel-induced NF-κB activation in breast cancer cells has not been shown before.

Figure 2:
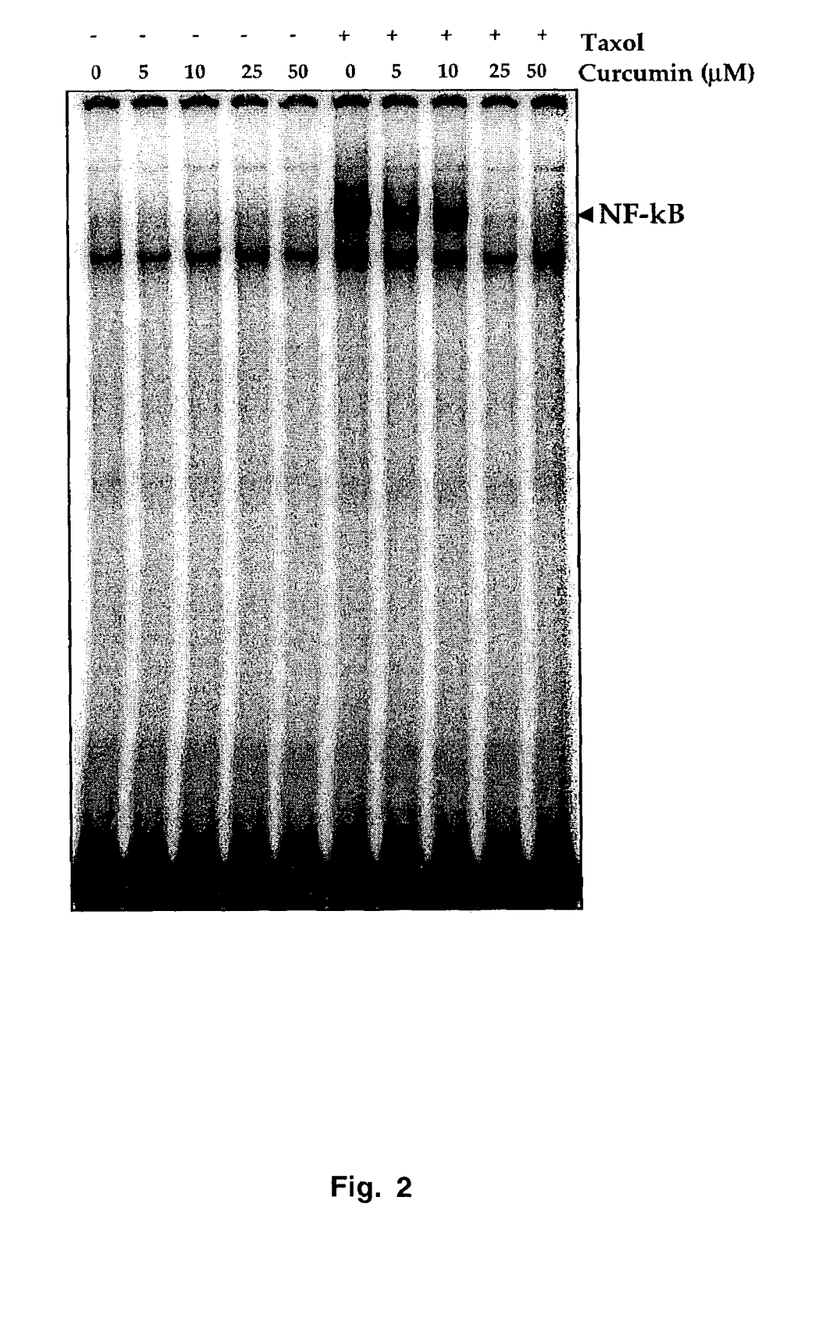
FIG. 2 shows curcumin downregulates taxol induced NF-κB induction in human breast adenocarcinoma MCF-7 cells. One million MCF-7 cells were pretreated with the indicated doses of curcumin for 2 hrs and then treated with taxol at 30 μM concentration for 12 hrs. Nuclear extract was prepared and EMSA performed using 8 μg of nuclear protein.
Figure 3:
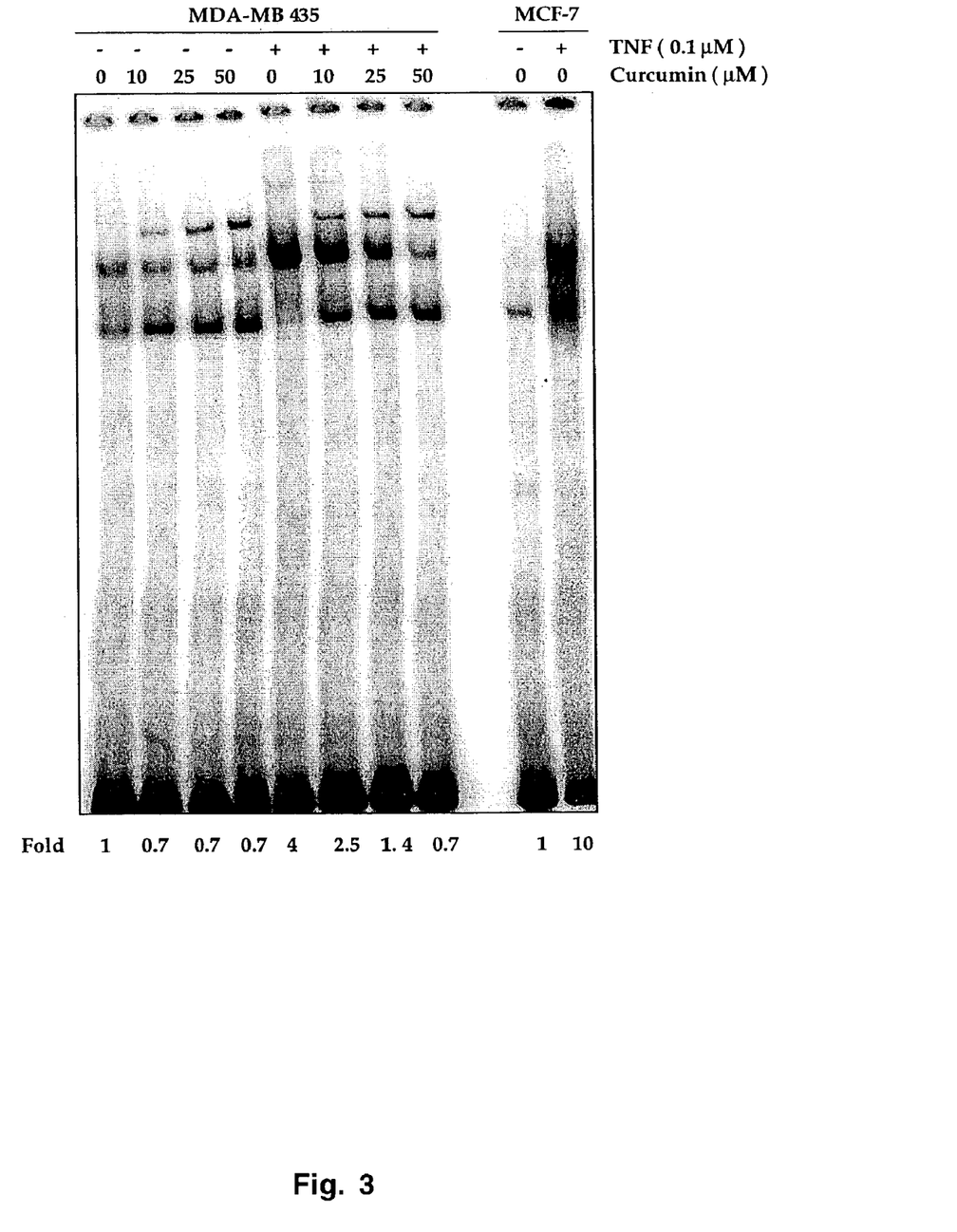
FIG. 3 shows the effect of curcumin on TNF dependent NF-κB activation. MDA-MB 435 cells ($1.5 \times 10^6$ cells/ml) were preincubated at 37° C. for 4 h with different concentrations (0 to 50 μM) of curcumin followed by 30 min incubation with 0.1 nM TNF. MCF-7 cells treated with 0 and 0.1 nM TNF was included as negative and positive control.

Human breast adenocarcinoma MCF-7 cells were pretreated with either media or different concentrations of curcumin (1–100 μM) for 2 h and then treated with paclitaxel for NF-κB activation. The nuclear extracts were prepared and analyzed by EMSA. The specificity of NF-κB can be examined by supershift analysis using antibodies against p50 and p65 subunits of NF-κB as described (109). As shown in FIG. 2, curcumin downregulated paclitaxel-induced NF-κB induction in MCF-7 cells in a dose dependent manner. Curcumin also inhibited TNF-dependent NF-κB activation in MDA-MB 435 cells (FIG. 3).

EXAMPLE 3

Suppression of Constitutive NF-κB Activation in Breast Cancer Cell Lines by Curcumin Several breast cancer lines are known to express constitutively active NF-κB. These include MDA-MB-436, HBL100, MDA-MB-468, MDA-MB-231 and MDA-MB-435 with highest expression; SK-BR-3 and ZR-75-1 with intermediate expression; and T47D and MCF-7 with lowest constitutive expression (34, 35).

Curcumin suppression of NF-κB in these cells can be examined by incubating the cells with curcumin at different concentrations and for different times. Their nuclear extracts can then be analyzed for NF-κB by EMSA.

EXAMPLE 4

The Mechanism by Which Curcumin Suppresses Paclitaxel-Induced or Constitutive NF-κB Activation Curcumin suppresses TNF-induced NF-κB activation through suppression of IκBα degradation (74). Others have shown that this suppression of NF-κB activation is mediated through suppression of IKK (75, 76), the kinase needed for IκBα phosphorylation. It is not known whether curcumin suppresses paclitaxel-induced NF-κB activation through similar mechanisms.

Whether curcumin suppresses paclitaxel-induced NF-κB activation in breast cancer cell lines through suppression of IκBα phosphorylation and degradation can be examined as follows. MCF-7 cells untreated or treated with curcumin can be activated for NF-κB with paclitaxel for different times, then their cytoplasmic extracts can be analyzed for degradation of IκBα by western blot analysis using IκBα-specific antibodies and for phosphorylated IκBα by western blot using phospho-IκBα-specific antibodies. IKK activity can be examined in the same cytoplasmic extracts as prepared above using immune complex kinase. Where in the paclitaxel-induced NF-κB activation pathway curcumin acts can be examined by NF-κB-dependent reporter gene transcription using procedures as described (112). In this system untreated or curcumin-treated cells are co-transfected with the plasmid containing known NF-κB signaling elements (such as TRAF2, NIK and IKK) and then examined for NF-κB activation.

EXAMPLE 5

Curcumin Enhances Paclitaxel-Induced Apoptosis and Suppresses NF-κB-Dependent Gene Expression Paclitaxel induces apoptosis of a wide variety of cells including breast cancer cells (9–11, 113, 114). Like other chemotherapeutic agents, paclitaxel also activates NF-κB (18–21, 115). Paclitaxel-failed to induce apoptosis in cells that express constitutive NF-κB or inducible NF-κB (28). Breast cancer cell lines (34, 35) and fresh breast cancer tissue samples express constitutive NF-κB (32, 33). Furthermore, paclitaxel-induced apoptosis in breast cancer cells is enhanced by suppression of NF-κB (31–32, 34, 36–37). Curcumin by itself inhibits the proliferation of breast cancer cells (63). The tumor promoter that activates NF-κB has been shown to block paclitaxel-induced apoptosis of breast cancer cells (116). Overexpression of HER2/neu, commonly associated with breast cancer, also suppresses paclitaxel-induced apoptosis (10, 11), and downregulation of HER2/neu by adenoviral E1A protein sensitizes breast cells to paclitaxel (117, 118). Because curcumin downregulates NF-κB activation, HER2/neu expression, AP-1/JNK, and expression of COX2 and cyclin D1 which are mechanisms that suppress apoptosis, it is possible that curcumin may have synergistic effects with paclitaxel in inducing apoptosis of breast cancer cells.

Figure 4:
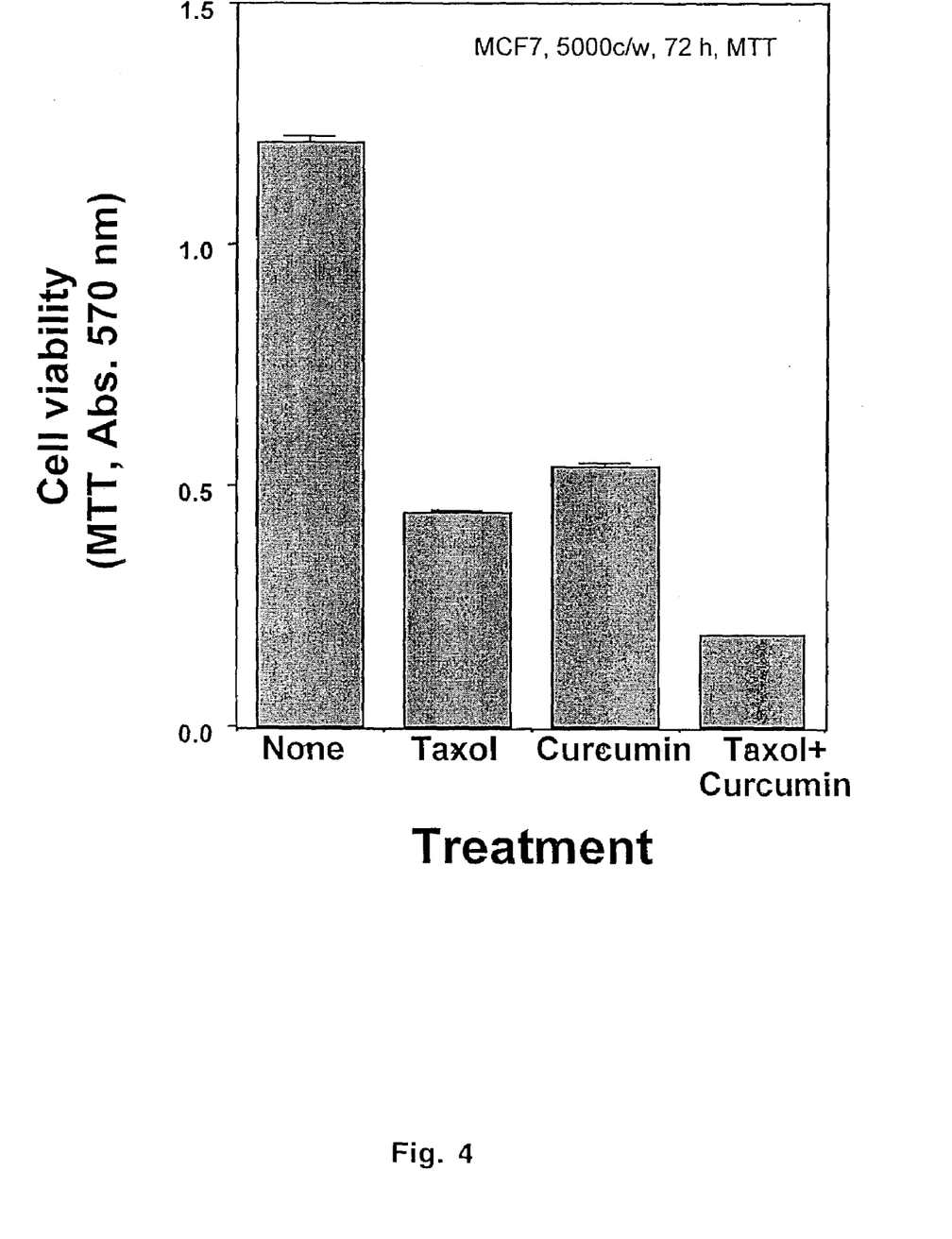
FIG. 4 shows that curcumin potentiates the cytotoxic effects of taxol against human breast cancer MCF-7 cells. 5000 cells were incubated with taxol (10 μM) in the presence and absence of curcumin (10 μM) for 72 h and then examined for cell viability by the MTT method.

Various breast cancer cell lines that express variable level of HER2/neu and NF-κB can be used to determine if curcumin augments paclitaxel-induced apoptosis in breast cancer cells. HER2/neu-positive (MDA-MB 453, BT-483, SKBR-3, MDA-MB361, BT-474) and HER2/neu-negative (MDA-MB435, MDA-MB231, MCF-7), as well as NF-κB positive (MDA-MB-436, HBL100, MDA-MB-468, MDA-MB-231, MDA-MB-435) and NF-κB negative (T47D and MCF-7) breast cancer cell lines can be examined for sensitivity to various concentrations of paclitaxel, curcumin, or combination of paclitaxel and curcumin for 24, 48 and 72 h, and then examined for viability by the MTT method as previously described (112, 119). FIG. 4 shows curcumin enhances the cytotoxic effects of paclitaxel against MCF-7 breast cancer cells.

To address the issue of whether curcumin suppresses paclitaxel-induced NF-κB-regulated gene expression, the cell lines indicated above are either left untreated or treated with paclitaxel, curcumin or combination of paclitaxel and curcumin for 6, 12, 24, and 48 h, and then the whole cell extracts can be analyzed by western blot analysis for expression of HER2/neu, COX2, MMP-9, iNOS, bcl-xl, bcl-2, cyclin D1, TRAF1, TRAF2, cIAP-1, cIAP-2, and XIAP using specific antibodies available commercially.

EXAMPLE 6

Curcumin Enhances the Therapeutic Effects of Paclitaxel against Breast Cancer In Vivo To optimize the therapeutic efficacy of paclitaxel, various agents have been employed in murine models harboring tumor xenografts. These include a protein tyrosine kinase inhibitor emodin (120), adenoviral protein E1A (117, 118), ras farnesyl transferase inhibitor (121), radioimmunotherapy with yttrium-90-labeled chimeric L6 antibody (122) and desoxyepothilone (123). Emodin was found to inhibit the growth of HER2/neu over-expressing tumors in mice, and sensitize the tumors to paclitaxel (120). Since emodin can block NF-κB activation (124), it is possible that some of the effects of emodin on paclitaxel are mediated through suppression of NF-κB activation.

Results shown above indicate curcumin enhances the cytotoxic effects of paclitaxel against human breast cancer cells in vitro. Since enhancement of in vitro cytotoxicity has been correlated with clinical responses to chemotherapy in breast cancer patients (125), it is believed that curcumin may augment the therapeutic efficacy of paclitaxel in a mouse model bearing a human tumor xenograft.

Moreover, angiogenesis plays a critical role in the growth and metastasis of solid tumors, including breast cancer (91). In addition to direct effects on tumor cell growth and survival, curcumin has been shown to be a potent anti-angiogenic factor (92–94). In animal studies, most investigators have employed curcumin to suppress tumor initiation and promotion and used 2% curcumin in the diet over long periods of time with no reported side effects (41–56).

To demonstrate that curcumin augments the therapeutic efficacy of paclitaxel in a mouse model bearing a human tumor xenograft, models of breast cancer in nude mice can be used (127). Human breast cancer cells (MDA-MB-231 or MDA-MB-435) that express constitutively active NF-κB can be injected into the mammary fatpad of female nude mice as previously described (127). Injection of human breast cancer cells into the mammary fatpad has been shown to promote the local growth, and for some tumors increases the incidence of distant metastasis, and is thus a suitable model for studying advanced stages of breast cancer (127). When the tumors are palpable (2–3 mm diameter, approximately 7–10 days after injection), the mice are divided into 4 treatment groups: (i) control diet, vehicle injection (i.p.); (ii) curcumin diet, vehicle injection (i.p.); (iii) control diet, Paclitaxel (10 mg/kg, i.p.); (iv) curcumin diet, Paclitaxel (10 mg/kg, i.p.).

Paclitaxel is prepared in a Cremophor:ethanol solution, and injected at 7-day intervals for up to 8 weeks. The tumors are measured twice weekly. At the end of the Paclitaxel therapy, sample mice from each group are killed and the tumors removed for measurement of NF-κB by immuno-histochemistry (with an antibody that can detect the active form translocated to the nucleus) and/or immunoblotting. Similarly, the expression of HER2/neu expression can also be examined. To show that the curcumin diet inhibits or retards the regrowth of the breast tumors after cessation of the Paclitaxel treatment, the remaining mice continue to eat the control or curcumin diet, and the size of the tumors are monitored. The end-point of the study is when the mammary fatpad tumors reach 1.5 cm diameter. To test whether the different treatments affect overall survival, the survival time of each mouse can be recorded and compared using a log rank analysis.

Figure 5:
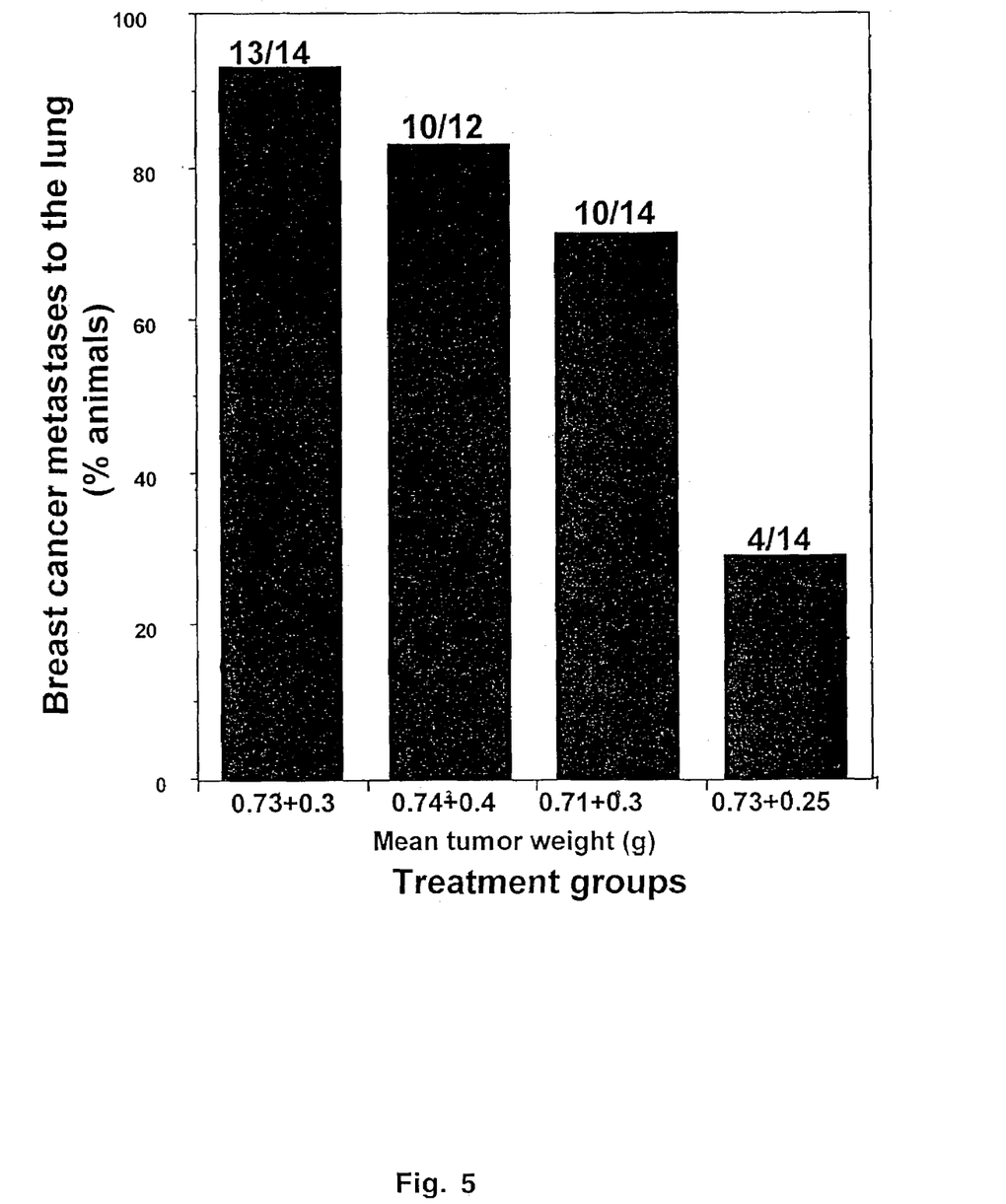
FIG. 5 shows that shows that curcumin potentiates the effect of paclitaxel by suppressing the metastasis of the human breast cancer to the lung in a mouse xenograft model.

To test whether curcumin alone, or in combination with Paclitaxel can suppress the growth of breast cancer metastases, the MDA-MB-435 breast cancer cells, which form distant metastases in nude mice following injection in the mammary fatpad, were used in a protocol designed to mimic clinical situation of treatment following removal of the primary tumor. Two millions MDA-MB-435 breast cancer cells were injected into the mammary fatpad of female nude mice. When the tumors reached 1 cm mean diameter, the mice were anesthetized, the tumors resected and the skin incision closed with wound clips. The mice were then be randomized into the same 4 treatment groups as described above to receive either curcumin diet, Paclitaxel injections, or curcumin diet plus-Paclitaxel injections. Paclitaxel was injected on day 10, 17 and 24 after tumor removal, and the mice were given diet containing 2% curcumin (w/w) 5 days after tumor removal. The treatment continue for up to 5 weeks after tumor removal, at which time the mice were killed and the number of visible metastases and presence of recurrent tumors or metastases in other organs were recorded. The lungs were fixed in 10% buffered formalin and paraffin-embedded section were stained with H&E to determine the incidence of micrometastases, or with antibodies recognizing the p65 subunit of NF-κB and HER2/neu. In previous therapy studies using this model of treatment following removal of 1 cm diameter tumors, the incidence of lung metastasis in the control groups was 80–100%. The significance of differences in the incidence of lung metastasis in the different groups was assessed using Fisher's exact test. Results in Table 1 and FIG. 5 indicate that curcumin enhances the effect of paclitaxel and suppresses breast cancer metastases to the lung.

TABLE 1

| Treatment and Group mets | Mean tumor Weight (g) | Incidence of macroscopic lung metastases | Median range of |
|---|---|---|---|
| Standard Diet/vehicle | 0.73 ± 0.3 | 93% | 12 (0–75) |
| Standard Diet/paclitaxel | 0.74 ± 0.4 | 83% | 20 (0–>100) |
| Curcumin/ vehicle | 0.71 ± 0.3 | 71% | 5 (0–44) |
| Curcumin/ Paclitaxel | 0.73 ± 0.25 | 29% | 0 (0–18) |

Fisher's exact test on incidence of macroscopic metastases:
A vs B p = 0.58
A vs C p = 0.326
A vs D p = 0.0013*
B vs D p = 0.0079*
C vs D p = 0.057
Mann-Whitney test for numbers of macroscopic metastases:
A vs B p = 0.772
A vs C p = 0.059
A vs D p = 0.0005*
B vs D p = 0.0034*
C vs D p = 0.029*

The following references are cited herein:
1. WHO. The world Health Report. Geneva:WHO.1997
2. Willett, J Intern Med., 249(5):395–411 (2001).
3. Carlson et al., Oncology (Huntingt), 10(11 Suppl):47–75 (1996).
4. Fabian, Breast Cancer Res., 3(2):99–103 (2001).
5. Kelloff, Advances in Cancer Research, 78:199–334 (2000).
6. el-Bayoumy,15(11):2395–420 (1994).
7. Russo and Russo, Oncol Res., 11(4):169–78 (1999).
8. Wall and Wani, J Ethnopharmacol. 51(1–3):239–53 (1996).
9. Rowinsky and Donehower, N Engl J Med. 332:1004–14 (1995).
10. Jing et al., Molecular Cell 2(5):581–91 (1998).
11. Yu et al., Oncogene 16(16):2087–94 (1998).
12. Blagosklonny and Fojo, Int J Cancer 83(2):151–6 (1999).
13. Liu et al., Biochem Pharmacol. 48(6):1265–72 (1994).
14. Schiff et al., Nature 277(5698):665–7 (1979).
15. Haldar et al., Cancer Res. 56(6):1253–5 (1996).
16. Poruchynsky et al., Cancer Res. 58(15):3331–8 (1998).
17. Fang et al., Anticancer Research 20(1A):103–11 (2000).
18. Perera et al., Infect Immun. 64(3):878–84 (1996).
19. Lee et al., Mol Cell Biol. 17(9):5097–105 (1997).
20. Collins et al., Cancer Immunol Immunother. 2000.
21. Huang et al., Cancer Research 60(16):4426–32 (2000).
22. Bogdan and Ding, J Leukocyte Biology. 52(1):119–21 (1992).
23. Singh et al., Cancer Research 54(12):3242–7 (1994).
24. Smith et al., J Exp Med. 179(5):1409–15 (1994).
25. Wang et al., Science, 274(5288):784–7 (1996).
26. Lee et al., J Exp Med., 181(3):1169–77 (1995).
27. Giri and Aggarwal, J Biol Chem. 273(22):14008–14 (1998).
28. Manna and Aggarwal, J Immunol. 162(3):1510–8 (1999).
29. Chen et al., Molecular & Cellular Biology 20(8):2687–95 (2000).
30. Amato et al., Cancer Research 58(2):241–7 (1998).
31. Clarkson et al., J Bio Chem. 275(17):12737–42 (2000).
32. Sovak et al., Cell Growth Differ. 10(8):537–44 (1999).
33. Sovak et al., J Clin Invest. 100(12):2952–60 (1997).
34. Cogswell et al., Oncogene 19(9):1123–31 (2000).
35. Nakshatri et al., Mol Cell Biol. 17(7):3629–39 (1997).
36. Patel et al., Oncogene 19(36):4159–69 (2000).
37. Newton et al., J Bio Chem. 274(26):18827–35 (1999).
38. Segev et al., J Bio Chem. 275(37):28371–9 (2000).
39. Zhou et al., J Bio Chem. 275(11):8027–31 (2000).
40. Ammon et al., Plant Med., 57: 1–7 (1991).
41. Huang et al., Carcinogenesis, 13: 2183–2186 (1992).
42. Huang et al., Cancer Res, 48: 5941–5946 (1988).
43. Conney et al., Adv. Enzyme Regul., 31: 385–396 (1991).
44. Lu et al., Carcinogenesis, 15(10):2363–70 (1994).
45. Limtrakul et al., Cancer Letters, 116(2):197–203 (1997).
46. Huang et al., Carcinogenesis, 18(1):83–8 (1997).
47. Huang et al., Cancer Research, 51(3):813–9 (1991).
48. Huang et al., Cancer Research, 54(22):5841–7 (1994).

49. Singh et al., Carcinogenesis, 19(8):1357–60 (1998).
50. Kim et al., Carcinogenesis, 19(1):81–5 (1998).
51. Rao et al., Cancer Research, 55(2):259–66 (1995).
52. Kawamori et al., Cancer Research, 59(3):597–601 (1999).
53. Chuang et al., Carcinogenesis, 21(2):331–5 (2000).
54. Singletary et al., Cancer Letters, 103(2):137–41 (1996).
55. Huang et al., Carcinogenesis, 19(9):1697–700 (1998).
56. Inano et al., Carcinogenesis, 20(6):1011–8 (1999).
57. Kuo et al., Biochimica et Biophysica Acta. 1317(2):95–100 (1996).
58. Ranjan et al., Journal of Surgical Research, 87(1):1–5 (1999).
59. Piwocka et al., Exp. Cell Research, 249(2):299–307 (1999).
60. Han et al., Clinical Immunology, 93(2):152–61 (1999).
61. Chen et al., Anticancer Research, 19(5A):3675–80 (1999).
62. Korutla and Kumar, Biochimica et Biophysica Acta. 1224(3):597–600 (1994).
63. Mehta et al., Anti-Cancer Drugs, 8:470–481 (1997).
64. Ramachandran and You, Breast Cancer Research & Treatment. 54(3):269–78 (1999).
65. Simon et al., Cancer Letters, 129(1):111–6 (1998).
66. Anto R. J., Mukhopadhyay A., Denning K., and Aggarwal B. B., Curcumin (Diferuloylmethane) Induces Apoptosis Through Activation of Caspase-8, BID cleavage and Cytochrome C Release: Its suppression by Ectopic Expression of Bcl-2 and Bcl-xL, *Carcinogenesis;* 23(1):143–50, 2002
67. Slamon et al., Science, 235(4785):177–82 (1987).
68. Korutla et al., Carcinogenesis, 16(8):1741–5 (1995).
69. Hong et al., Clinical Cancer Research, 5(7):1884–91 (1999).
70. Mukhopadhyay A, Bueso-Ramos C, Chatterjee D, Pantazis P and Aggarwal B B: Curcumin Downregulates Cell Survival Mechanisms in Human Prostate Cancer Cell Lines. *ONCOGENE* 20, 7597–7609, 2001
71. Baldwin, J Clin Invest., 107(3):241–6 (2001).
72. Pahl, Oncogene, 18(49):6853–66 (1999).
73. Kim et al., Carcinogenesis, 21(5):871–9 (2000).
74. Singh and Aggarwal, J Bio Chem. 270(42):24995–5000 (1995).
75. Jobin et al., J Immunol. 163(6):3474–83 (1999).
76. Plummer et al., Oncogene 18(44):6013–20 (1999).
77. Karin et al., Curr Opin Cell Biol. 1997.
78. Xia et al., Proc Natl Acad Sci USA. 97(10):5243–8 (2000).
79. Huang et al., J Biol Chem. 274(42):29672–6 (1999).
80. Huang et al., Proc Natl Acad Sci USA. 88(12):5292–6 (1991).
81. Chen and Tan, Oncogene 17(2):173–8 (1998).
82. Ohene-Abuakwa and Pignatelli, Adv Exp Medicine & Biology 465:115–26 (2000).
83. Iademarco et al., J Clinical Invest. 95(1):264–71 (1995).
84. Kumar et al., Biochemical Pharmacology 55(6):775–83 (1998).
85. Fournier and Gordon, J Cell Biochem. 77(S34):97–1021 (2000).
86. Hida et al., Cancer Res. 58(17):3761–4 (1998).
87. Harris et al., Cancer Research 60(8):2101–3 (2000).
88. Williams et al., Oncogene 18(55):7908–16 (1999).
89. Reddy et al., Cancer Res. 60(2):293–7 (2000).
90. Zhang et al., Carcinogenesis 20(3):445–51 (1999).
91. Folkman, Proc Natl Acad Sci USA. 98(2):398–400 (2001).
92. Singh et al., Cancer Letters 107(1):109–15 (1996).
93. Mohan et al., J Bio Chem. 275(14):10405–12 (2000).
94. Arbiser et al., Molecular Medicine 4(6):376–83 (1998).
95. Kumar et al., FEBS Letters 462(1–2):140–4 (1999).
96. Lin et al., Oncology 55(4):349–53 (1998).
97. Pan et al., Biochemical Pharmacology 60(11):1665–76 (2000).
98. Menon et al., Cancer Letters 141(1–2):159–65 (1999).
99. Weinstat-Saslow et al., Nat Med. 1(12):1257–60 (1995).
100. Wang et al., Nature 369:669–71 (1994).
101. Sicinski et al., Cell 82(4):621–30 (1995).
102. Lee et al., Mol Cell Biol. 20(2):672–83 (2000).
103. Sauter et al., Cancer Res. 59(19):4876–81 (1999).
104. Langenfeld et al., PNAS. 94(22):12070–4 (1997).
105. Guttridge et al., Mol Cell Biol. 19(8):5785–99 (1999).
106. Karin, Oncogene 18(49):6867–74 (1999).
107. Mukhopadhyay et al., J Biol Chem. 275(12):8549–55 (2000).
108. Bonizzi et al., J. Immunol. 159: 5264 (1997).
109. Chaturvedi et al., Methods Enzymol. 319:585–602 (2000).
110. Manna et al., J Immunol. 165(9):4927–34 (2000).
111. Darnay et al., J Bio Chem. 274(12):7724–31 (1999).
112. Manna et al., Cancer Res. 60(14):3838–47 (2000).
113. Saunders et al., Intl J Cancer 70(2):214–20 (1997).
114. McCloskey et al., Clinical Cancer Research 2:847–54 (1996).
115. Das and White, J Bio Chem. 272(23):14914–20 (1997).
116. Shen et al., Cell Growth & Differentiation 9(1):23–9 (1998).
117. Zhang et al., Oncogene 10(10):1947–54 (1995).
118. Ueno et al., Oncogene 15(8):953–60 (1997).
119. Rubinstein et al., J Natl Cancer Institute 82(13):1113–8 (1990).
120. Zhang et al., Clinical Cancer Research 5(2):343–53 (1999).
121. Moasser et al., Proc Natl Acad Sci USA. 95(4):1369–74 (1998).
122. DeNardo et al., Proc Natl Acad Sci USA. 94(8):4000–4 (1997).
123. Chou et al., Proc Natl Acad Sci USA. 95(26):15798–802 (1998).
124. Kumar et al., Oncogene 17:913–918 (1998).
125. Agiostratidou et al., Anticancer Research 21(1A):455–9 (2001).
126. Hata et al., Oncology Research 6(1):19–24 (1994).
127. Price et al., Cancer Research 50(3):717–21 (1990).
128. Glinsky et al., Cancer Research 56(23):5319–24 (1996).

Any patents or publications mentioned in this specification are indicative of the levels of those skilled in the art to which the invention pertains. Further, these, patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes to this invention and other uses will occur to those skilled in the art which are encompassed within the spirit of the invention as defined by the scope of the claims.

What is claimed is:

1. A method of inhibiting metastasis of a tumor in an individual in need of such treatment, comprising the step of administering to said individual a pharmacologically effective dose of an inhibitor of the activation of nuclear factor NF-κB and a cancer chemotherapeutic agent, wherein the dose of the inhibitor of activation of nuclear factor NF-κB and the cancer chemotherapeutic agent together is pharmacologically effective to inhibit metastatis of the tumor.

2. The method of claim 1, wherein said inhibitor of the activation of nuclear factor NF-κB is selected from the group consisting of a curcuminoid, CAPE, capsaicin, sanguinarin, PTPase inhibitors, lapachone, resveratrol, vesnarinone, leflunomide, anethole, PI3 kinase inhibitors, oleanderin, emodin, serine protease inhibitors, protein tyrosine kinase inhibitors, thalidomide and methotrexate.

3. The method of claim 2, wherein said inhibitor of the activation of nuclear factor NF-κB is a curcuminoid which is administered in a dose of from about 10 mg/kg to about 1000 mg/kg.

4. The method of claim 1, wherein said tumor is selected from the group consisting of a breast tumor, prostate, melanoma, pancreas, colon, leukemia and multiple myeloma.

5. The method of claim 1, wherein said cancer chemotherapeutic agent is selected from the group consisting of paclitaxel, gemcitabin, 5-flurouracil, etoposide, cispaltin, campothecin, vincristine and doxorubicin.

6. A method of treating a tumor in an individual in need of such treatment, comprising the step of administering to said individual a pharmacologically effective dose of an inhibitor of the activation of nuclear factor NF-κB and a cancer chemotherapeutic agent, wherein the dose of the inhibitor of activation of nuclear factor NF-κB and the cancer chemotherapeutic agent together is pharmacologically effective to treat the tumor in the individual.

7. The method of claim 6, wherein said inhibitor of the activation of nuclear factor NF-κB is selected from the group consisting of a curcuminoid, CAPE, capsaicin, sanguinarin, PTPase inhibitors, lapachone, resveratrol, vesnarinone, leflunomide, anethole, PI3 kinase inhibitors, oleanderin, emodin, serine protease inhibitors, protein tyrosine kinase inhibitors, thalidomide and methotrexate.

8. The method of claim 7, wherein said inhibitor of the activation of nuclear factor NF-κB is a curcuminoid which is administered in a dose of from about 100 mg/kg to about 1000 mg/kg.

9. The method of claim 6, wherein said tumor is selected from the group consisting of a breast tumor, prostate, melanoma, pancreas, colon, leukemia and multiple myeloma.

10. The method of claim 6, wherein said cancer chemotherapeutic agent is selected from the group consisting of paclitaxel, gemcitabin, 5-flurouracil, etoposide, cisplatin, campothecin, vincristine and doxorubicin.

11. A method of inhibiting metastasis of a tumor in an individual in need of such treatment, comprising the step of administering to said individual a pharmacologically effective dose of a curcuminoid and a cancer chemotherapeutic agent, wherein the dose of the curcuminoid and the cancer chemotherapeutic agent together is pharmacologically effective to inhibit metastatis of the tumor.

12. The method of claim 11, wherein said dose of a curcuminoid is from about 10 mg/kg to about 1000 mg/kg.

13. The method of claim 11, wherein said tumor is selected from the group consisting of a breast tumor, prostate, melanoma, pancreas, colon, leukemia and multiple myeloma.

14. The method of claim 11, wherein said cancer chemotherapeutic agent is selected from the group consisting of paclitaxel, gemcitabin, 5-flurouracil, etoposide, cisplatin, campothecin, vincristine and doxorubicin.

15. A method of treating a tumor in an individual in need of such treatment, comprising the step of administering to said individual a pharmacologically effective dose of a curcuminoid and a cancer chemotherapeutic agent, wherein the dose of the curcuminoid and the cancer chemotherapeutic agent together is pharmacologically effective to treat the tumor in the individual.

16. The method of claim 15, wherein said dose of a curcuminoid is administered in a dose of from about 10 mg/kg to about 1000 mg/kg.

17. The method of claim 15, wherein said tumor is selected from the group consisting of a breast tumor, prostate, melanoma, pancreas, colon, leukemia and multiple myeloma.

18. The method of claim 15, wherein said cancer chemotherapeutic agent is selected from the group consisting of paclitaxel, gemcitabin, 5-flurouracil, etoposide, cispaltin, campothecin, vincristine and doxorubicin.

19. A method of inhibiting metastasis of a breast tumor in an individual in need of such treatment, comprising the step of administering to said individual a pharmacologically effective dose of a curcuminoid and a cancer chemotherapeutic agent, wherein the dose of curcuminoid and the cancer chemotherapeutic agent together is pharmacologically effective to inhibit metastatis of the breast tumor.

20. The method of claim 19, wherein said dose of a curcuminoid is administered in a dose of from about 10 mg/kg to about 1000 mg/kg.

21. The method of claim 19, wherein said cancer chemotherapeutic agent is selected from the group consisting of paclitaxel, gemcitabin, 5-flurouracil, etoposide, cisplatin, campothecin, vincristine and doxorubicin.

22. A method of treating breast tumor in an individual in need of such treatment, comprising the step of administering to said individual a pharmacologically effective dose of a curcuminoid and a cancer chemotherapeutic agent, wherein the dose of the curcuminoid and the cancer chemotherapeutic agent together is pharmacologically effective to treat the breast tumor in the individual.

23. The method of claim 22, wherein said dose of a curcuminoid is administered in a dose of from about 10 mg/kg to about 1000 mg/kg.

24. The method of claim 22, wherein said cancer chemotherapeutic agent is selected from the group consisting of paclitaxel, gemcitabin, 5-flurouracil, etoposide, cisplatin, campothecin, vincristine and doxorubicin.

* * * * *

SEQUENCE LISTING

<160> NUMBER OF SEQ ID NOS: 1

<210> SEQ ID NO 1
<211> LENGTH: 11
<212> TYPE: DNA
<213> ORGANISM: Artificial sequence
<220> FEATURE:
<221> NAME/KEY:
<223> OTHER INFORMATION: specific sequence within the immunoglobulin light chain ( locus enhancer region

<400> SEQUENCE: 1
ggggactttc c                                                                 11